United States Patent
Ferreira et al.

(10) Patent No.: US 6,525,173 B1
(45) Date of Patent: Feb. 25, 2003

(54) PROCESS FOR EXPRESSION AND PRODUCTION OF RECOMBINANT PROTEIN HYBRID PROTEIN (P24/P17) DERIVED FROM HUMAN IMMUNODEFICIENCY VIRUSES (HIV-1)

(75) Inventors: Paulo Cesar Peregrino Ferreira, Belo Horizonte (BR); Erna Geessien Kroon, Belo Horizonte (BR)

(73) Assignee: Universidade Federal de Minas Gerais, Minas Gerais (BR)

( * ) Notice: Subject to any disclaimer, the term of this patent is extended or adjusted under 35 U.S.C. 154(b) by 0 days.

(21) Appl. No.: 09/142,141

(22) PCT Filed: Dec. 30, 1997

(86) PCT No.: PCT/BR97/00085

§ 371 (c)(1),
(2), (4) Date: May 12, 1999

(87) PCT Pub. No.: WO98/29551

PCT Pub. Date: Jul. 9, 1998

(30) Foreign Application Priority Data

Jan. 2, 1997 (BR) .............................. 9700858

(51) Int. Cl.[7] .................. A61K 39/21; C07H 21/00; C07K 14/16; C12N 5/06; C12N 7/04

(52) U.S. Cl. ................. 530/350; 424/208.1; 424/188.1; 424/192.1; 435/7.1; 435/69.1; 435/69.3; 435/70.1; 435/71.1; 435/71.2; 435/235.1; 435/320.1; 514/44; 536/23.72

(58) Field of Search ............................ 424/208.1, 188.1, 424/192.1; 435/7.1, 69.1, 69.3, 70.1, 71.1, 71.2, 235.1, 320.1; 514/44; 530/350; 536/23.72

(56) References Cited

U.S. PATENT DOCUMENTS

| 4,808,536 A | * | 2/1989 | Chang et al. |
| 4,918,166 A | * | 4/1990 | Kingsman et al. |
| 5,041,385 A | | 8/1991 | Kingsman et al. |
| 5,310,876 A | * | 5/1994 | Bayer et al. |
| 5,463,024 A | | 10/1995 | Kingsman et al. |
| 5,576,421 A | * | 11/1996 | Saito et al. |

FOREIGN PATENT DOCUMENTS

| EP | 0552850 A1 | * | 10/1985 |
| EP | 0230222 A1 | * | 7/1987 |
| WO | 88/03562 | | 5/1988 |
| WO | WO95/16040 | * | 6/1995 |

OTHER PUBLICATIONS

Cell, vol. 53, No. 1, Apr. 8, 1988, J.M. McCune et al.: "Endoproteolytic Cleavage of gp160 Is Required for the Activation of Human Immunodeficiency Virus", pp. 55–67.

* cited by examiner

Primary Examiner—Phuong T. Bui
(74) Attorney, Agent, or Firm—Young & Thompson

(57) ABSTRACT

The present invention describes recombinant p24/p17 hybrid protein derived from the human immunodeficiency virus, their corresponding encoding recombinant DNA molecule and the process of production of the recombinant protein produced through genetic engineering techniques, to be used in diagnosis, vaccination or in research.

1 Claim, 4 Drawing Sheets

Figure 2

GluAlaLeuAspLysIleGluGluGluGln.AsnLysSerLysLysLysAlaGlnGlnAla
AlaAlaAspThrGlyHisSerSerGlnVal.SerGlnAsnTyrProIleValGlnAsnIle
GlnGlyGlnMetValHisGlnAlaIleSer.ProArgThrLeuAsnAlaTrpValLysVal
5   ValGluGluLysAlaPheSerProGluVal.IleProMetPheSerAlaLeuSerGluGly
AlaThrProGlnAspLeuAsnThrMetLeu.AsnThrValGlyGlyHisGlnAlaAlaMet
GlnMetLeuLysGluThrIleAsnGluGlu.AlaAlaGluTrpAspArgValHisProVal
HisAlaGlyProIleAlaProGlyGlnMet.ArgGluProArgGlySerAspIleAlaGly
ThrThrSerThrLeuGlnGluGlnIleGly.TrpMetThrAsnAsnProProIleProVal
10  GlyGluIleTyrLysArgTrpIleIleLeu.GlyLeuAsnLysIleValArgMetTyrSer
ProThrSerIleLeuAspIleArgGlnGly ProLysGluProPheArgAspTyrVal

Hydrophilicity profile of protein sequence P1724
Computed using an average group length of 6 amino acids.

SEQUENCE LISTING

```
<160> NUMBER OF SEQ ID NOS:  5

<210> SEQ ID NO 1
<211> LENGTH: 27
<212> TYPE: DNA
<213> ORGANISM: Human immunodeficiency virus

<400> SEQUENCE: 1
ggatccccgc tgacatggag caaggcg                                27

<210> SEQ ID NO 2
<211> LENGTH: 25
<212> TYPE: DNA
<213> ORGANISM: Human immunodeficiency virus

<400> SEQUENCE: 2
cgcgaagctt caggctccat ctgtc                                  25

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: PCT, primer
      of the vector
<221> NAME/KEY: primer_bind
<222> LOCATION: (1)..(20)
<223> OTHER INFORMATION: Sense primer

<400> SEQUENCE: 3
ttcattaaag aggagaaatt                                        20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: PCT, primer
      of the vector
<221> NAME/KEY: primer_bind
<222> LOCATION: (1)..(20)
<223> OTHER INFORMATION: Anti-sense primer

<400> SEQUENCE: 4
ctatcaacag gagtccaagc                                        20

<210> SEQ ID NO 5
<211> LENGTH: 199
<212> TYPE: PRT
<213> ORGANISM: Human immunodeficiency virus
```

<400> SEQUENCE: 5

```
Glu Ala Leu Asp Lys Ile Glu Glu Gln Asn Lys Ser Lys Lys Lys
 1               5                  10                  15

Ala Gln Gln Ala Ala Ala Asp Thr Gly His Ser Ser Gln Val Ser Gln
                20                  25                  30

Asn Tyr Pro Ile Val Gln Asn Ile Gln Gly Gln Met Val His Gln Ala
            35                  40                  45

Ile Ser Pro Arg Thr Leu Asn Ala Trp Val Lys Val Val Glu Glu Lys
        50                  55                  60

Ala Phe Ser Pro Glu Val Ile Pro Met Phe Ser Ala Leu Ser Glu Gly
65                  70                  75                  80

Ala Thr Pro Gln Asp Leu Asn Thr Met Leu Asn Thr Val Gly Gly His
                85                  90                  95

Gln Ala Ala Met Gln Met Leu Lys Glu Thr Ile Asn Glu Glu Ala Ala
                100                 105                 110

Glu Trp Asp Arg Val His Pro Val His Ala Gly Pro Ile Ala Pro Gly
            115                 120                 125

Gln Met Arg Glu Pro Arg Gly Ser Asp Ile Ala Gly Thr Thr Ser Thr
130                 135                 140

Leu Gln Glu Gln Ile Gly Trp Met Thr Asn Asn Pro Pro Ile Pro Val
145                 150                 155                 160

Gly Glu Ile Tyr Lys Arg Trp Ile Ile Leu Gly Leu Asn Lys Ile Val
                165                 170                 175

Arg Met Tyr Ser Pro Thr Ser Ile Leu Asp Ile Arg Gln Gly Pro Lys
            180                 185                 190

Glu Pro Phe Arg Asp Tyr Val
            195
```

PROCESS FOR EXPRESSION AND PRODUCTION OF RECOMBINANT PROTEIN HYBRID PROTEIN (P24/P17) DERIVED FROM HUMAN IMMUNODEFICIENCY VIRUSES (HIV-1)

TECHNICAL FIELD OF THE INVENTION

The present invention refers to the general field of the technology of the DNA recombinant proteins, for the production of a recombinant hybrid protein (p24/p17) derived from human immunodeficiency virus (HIV-1) to be used in diagnosis of acquired immunodeficiency disease virus (AIDS), vaccination, antibody production or in research.

BACKGROUND TO THE INVENTION

The epidemic provoked by the human immunodeficiency virus(HIV), today global, continues without bamers, and has as a consequence the syndrome of the acquired immunodeficiency(AIDS), recognized 12 years ago. The studies of the World Organization of Health estimated that more than 18 million people are infected and by the year 2000, 40 to 100 million people worldwide would have been infected by HIV-1 or HIV-2, from which 10 million will be children.

The hope for an effective therapy and, mainly, the prevention resides in the acquisition of new information on the virus, the mechanisms of the pathogenesis and in the search of experimental models (COOPER. Immunol. 4: 461, 1992). The current knowledge is that blocking the dissemination will be very important and therefore the early detection is needed for the treatment with the new drugs.

The virus concentration can greatly influenced the virus transmission in a body fluid. In the beginning of the epidemic the major routes of AIDS transmission were sexual contact and through transfusion with contaminated blood (Levis in: HIV and pathogenesis of AIDS p.26,1989). The syndrome was initially described in homosexual and bisexual men and in intravenous drug users (Mansur et al.,N. Engl. J. Med.305:1431,1989, but its occurrence from heterosexual activity were soon recognized (Harris, C et al., N.Engl. J. Med.308:1181,1983). Today the principal means of transmission are the sexual, maternal-child, drug users and still blood in undeveloped countries. All of them can be explained to a great extent by the relative concentration of HIV in various body fluids.

HIV entry in the body and developed acute infection as observed by other virus. The HIV pathogenesis reflects several properties of the virus and the host immune response. AIDS final outcome is the differential expression of those major components of HIV infection The first step of HIV infection is the interaction between the major lymphocyte receptor CD4 molecule, a member of immunoglobulin superfamily with the envelope gp120 protein. According to some reports described gp 120 is displaced, leading to the uncovering of domain on the envelope gp41 needed for virus cell fusion. Once in the cytoplasm several intracellular events take place ending with integration of a proviral form into cellular genome.

Besides entering cells via the direct interaction of the virus envelope with cell surface receptors, HIV can infect cells by other mechanisms. For example, during the course of studies on the humoral response to HIV-1 (infection, the phenomenon of antibody dependent enhancement (ADE), of HIV infection was found to occur (Homsy, J. et al. Science 244: 1357, 1989; Homsy, J. et al. Lancet i: 1285, 1988). The transfer of the virus into a cell through the complement or Fc receptor involves the binding of the Fab portion of nonneutralizing antibodies to the virus surface (Levy in: HIV and the pathogenesis.p.53,1994)

Clinical manifestations of acute HIV infection were recognized in the very early studies, and have been described in various articles (Thindall and Cooper, AIDS:5:1, 1991; NIV, MT et al. J. Infect. Dis. 168:1490, 1993). A newly infected host present within 1 to 3 weeks symptoms as headache, pain, muscle aches, sore throat, fever, swollen lymph nodes, a non pruritic macular erythematous rash involving the trunk and later the extremities.

It is estimated that 50 to 70% of patients primary infected with HIV will developed a syndrome of acute mononucleosis-like illness. This period is associated with high viremia levels, and the immune humoral response against the virus is detected between one week and three months (DAAR et al. New Engl. J. Med 324: 961,1991).

This specific immunity that initiates in this period is associated to a dramatic decline of the viremia, but the level of this immunity inadequate to suppress the viral multiplication. The expression of the virus persists in the lymph nodes, even when the presence of the virus in the plasma is difficult to be detected, and the mRNA is not detectable in the mononuclear cells of blood stream (MICHAEL et al. J. Virol. 66: 310–316, 1992).

HIV is classified, based on its morphology, genomic organization and pathogenic properties, as a member of the sub-family lentivirus of the family Retrovindae.

HIV-1 and HIV-2 as a lentivirus have the characteristic cone-shaped core composed of the viral p24 GAG protein. Inside this capsid are two identical RNA strands with the reverse transcriptase (RNA dependent DNA polymerase) and the nucleocapsid proteins (p9, p6) are closely associated. The inner portion of the viral membrane is surrounded by a myristylated p17 core protein (GAG) that provides the matrix (MA) for the viral structure which is important for virion integrity (McCune, J. M. et al. Cell 53: 55, 1988; Shulz, T. F. et al. AIDS Res. Human Retrov 8:1584, 1992). The virus surface is made by envelope glycoproteins derived from a precursors of Mw 160.000 which is inserted inside the cell into a gp120 and a gp41 transmembrane protein (TM). The central region of TM protein binds to the external viral gp120 in a non covalent ligation at two hydrophobic regions in the amino and carboxi termini of gp120 (Helseth, E. et al. J.Virol. 65:2119–2123, 1991.

Two other genes tat and rev are positive regulators for the replication of HIV, besides other proteins with accessory function, as the vpu, vif, vpr and nef (ROSEN, TIG 7: 9–14. 1991.).

One of the most notable properties of the genoma of the HIV-1 is its genetic variation (DESAI et al Proc. Natl. Acad. Sci. 83: 8380, 1986). The diversity can be important for many aspects of the biology of the virus, among them the tissue and cell specificity, clinical-pathological picture of the disease, geographical and temporary virus distribution, difference in the susceptibility of immune response, virulence and, especially, development of a vaccine of wide crossed reactivity. The mistake range esteemed for the variation of HIV is of a substitution in $10^4$ synthesized nucleotides. Besides the substitution, deletions and inserts, whose frequency is more difficult of being evaluated can happen.

The gene env shows, along its structure, variable (V) and constant (C) regions. The principal neutralizing domain of the HIV-1 is placed in the third variable region (it raises V3)

of the envelop glycoprotein (gp120). The loop V3 is an important neutralization epitop for, viral tropism and syncytium formation. In the V3 loop is the neutralyzing epitop for type-specific antibodies.

The laboratory diagnosis of any infectious agent is an important aspect for the control of infectious diseases. The precise diagnosis wins importance in the blood derivatives, whose use depends on the capacity of the tests in the detection of infectious agents' or its antigens. During the last decade, the technological progresses developed precise tests for the diagnosis of AIDS. Most of the researches concentrated efforts for the development of tests to be used in development countries were are the economic limitation. In those countries the HIV detection is not a routine.

The HIV-1 diagnosis is made with the indirect detection of the presence of the virus, indicated by the patient's immune response, evidenced by the presence of specific antibodies against the HIV-1 or the detection of the virus or its components.

The direct methods identify the virus multiplication in culture, detection of virus or antigens in immunoassays (ELISA), molecular hybridization or amplification of nucleic acids (PCR). However, some of these tests demand qualified personnel and equipped laboratories, what hinders its widespread use. An exception is the test of ELISA for the antigen p24, that can be detected in patients before the detection of antibodies, even so, in some cases, it is only detected in late infections and in some patient were it seems to be transient. Thus, the negative result of tests for HIV-1 antigens is not informative and it doesn't necessarily reflect a not infected individual (BYLUND et al. Clin. Lab. Med. 12: 305, 1992)

THE indirect methods determine the detection of antibodies. However, these antibodies are detected a time after infection from six weeks to six months.

Other indirect tests are those that not measure specific immune response but some proteins as β-2-microglobulina and neopterine, that indicate the activation of the immune response.

The detection of HIV-1 antibodies is the most used and efficient method to demonstrate the patient's contact with the virus or to verify the contamination of blood samples. In 1988, laboratories linked to the program Performance Evaluation Program of the Center of Control of Diseases (CDC, Atlanta, USA), evaluated around 32 million tests using antibody anti-HIV. A test of antibody anti-HIV is considered positive, when a sequence of tests, beginning with repeated ELISA and including additional, more more specific test, as the Western blot, they are consistently positive (CDC, MMWR ,1987). (BYLUND et al. Clin. Lab. Med. 12: 305, 1992).

The ELISA test is most used for detection of the HIV-1 because of the low cost, easy standardization and execution, Initially, it was licensed, in 1985, to test blood donors and blood products, being their use expanded to determine antibodies anti-HIV-1 in populations (Weiss et al. JAMA 253: 221, 1985). Several studies described the high sensibility of this test from 93% to 100% (BYLUND et al. Clin. Lab. Med. 12: 305, 1992).). Several kits of ELISA were licensed by the "Food and Drug Administration " (FDA), in United States. Most of the tests used inactivated and purified lysates of T cell lineage, H-9, as source of antigen, that is rich in p24 and p17 antigens, with some loss of gp160, gp120 and p41 during the preparation. The contamination of the preparations of antigens with cell debris can originate the false positive result, due to cross reactions. These problems were now resolved with the use of recombinant antigens or synthetic peptides in the tests of ELISA, that constitute the last generation of tests to detect the antibody anti-HIV.

The recombinant proteins produced in bacterias and yeasts has been used as antigen for different types of tests, like ELISA, radioimmunoprecipitation, latex agglutination and Western blot. The sensibility and the specificity of these methods are excellent (99 to 100%), and they can detect the serum conversion earlier than ELISA that uses antigens of total virus.

The Western blot is the most used complementary test for the detection of specific antibody anti-HIV-1. In comparison to ELISA the Western blot is of higher cost and it requests technical personnel specialized due to subjective interpretation, because a universal approach doesn't exist for the interpretation of positive cases.

The bands of gp120 and gp41 don't have a good resolution, because these are glycosilated proteins of the envelope that migrates slowly in the gel, being considered an only band, for the interpretation of the results. A negative test is doesn't present any band, however the presence of an only band doesn't fill the requirements for a positive test and it is considered uncertain. This approach perhaps is not ideal to be used patients of high risk, or for patients with suggestive symptoms of HIV infection, especially if the band of p24 is detected (KLEINMAN. Arch. Pathol. Lab. Med., v.114, p.298, 1990.).

The false positive reactions can be observed in the ELISA test in the early and late phases of the patient's infection by HIV-1. False-positive results were described in patients with hiperbilirubinemie, disorders of the connective tissue, polyclonal gamopatias, besides in healthy individuals, as a result of a not very understood cross-reaction. However, it was verified that, in a population of low risk, the index of false-positive reactions of the tests of ELISA and Western blot combined was smaller than $10^{-5}$ (BURKE et al., New Engl. J. Med. 319: 961. 1988).

Thus, there is need of a system with high sensibility for the detection of the virus, its components or antibodies from infected individuals' An important fact is it that the synthetic peptides and recombinant proteins are superior to the antigens from cell lysates. Thus, through the genetic engineering, it is possible to construct hybrid proteins that combine antigenic characteristic of more than one viral component.

It is object of the present invention to describe the recombinant hybrid p24/p17 protein of HIV-1, their corresponding encoding recombinant DNA molecule and the process of production of the recombinant hybrid p24/p17 protein of HIV-1 produced through techniques of genetic engineering, to be used for diagnosis, vaccination or in research.

BRIEF DESCRIPTION OF THE DRAWINGS

These and other objects, features and many attendant advantages of the invention will be better understood upon a reading of the following detailed description when considered in connection with the accompanying drawings wherein:

FIG. 2 shows the amino acid sequence of the recombinant hybrid p24/p17 protein of HIV-1

DETAILED DESCRIPTION OF THE INVENTION

The methodology used for the production of the recombinant hybrid p24/p17 protein of HIV-1consists of the cloning and expression, in microorganisms, of the DNA corresponding to the gene that codes recombinant hybrid p24/p17 protein of HIV-1 using the methodology of the genetic engineering.

In order to better understand this invention the following examples, for illustrative purposes only, are described. The examples illustrate the present invention and are not intended to limit it in spirit or scope. The process can be understood better through the following description in consonance with the examples.

EXAMPLE 1

Amplification of the DNA (1)

The amplification of the DNA (1) derived from the proviral DNA, or starting from the vector that contains the cloned DNA of the gene for P-24/p17 hybrid protein was developed using specific oligonucleotides 5' GGATC-CCCGCTGACATGGAGCAAGGCG3 (SEQ ID NO. 1) and 5' CGCGAAGCTTCAGGCTCCATCTGTC3' (SEQ ID NO. 2). Those oligonucleotides were drawn to amplify, through polymerase chain reaction (PCR), the DNA region that encodes the corresponding fragment of the P-24/p17 hybrid protein. The primers also contains the sites for the restriction enzymes BamH-1 and Hind III.

The PCR reaction was performed by using Taq polymerase buffer (50 mM KCI, 100 mM Tris-HCI pH 9.0–9.5, 1.5–2.5 mM $MgCI_2$ and 1–2% triton X-100), 0.1–1 U of Taq polymerase (Promega ,E.U.A., Cat. no. M186A), 0.5–1.5 mM $MgCI_2$, 20–50 mM of each nucleotide (dATP,dCTP, dGTP,dTTP) 10–30 umoles of each primer, and 0.01a 0.1 μg cDNA and $H_2O$ q.s.p. 50–100 μl. The reaction was performed in 1–2 cycles at 94–96° C./1–2 min; 53 to 55° C. 1–2 min.; 70–72° C./1–2 min; 30 cycles at 94–96° C./1 to 2min; 36–38° C./1–2min; 70–72° C./1–2 min and more 1 cycle to 94–96° C./1–2 min; 36–38° C./1 to 2 min; 70–72° C./10–15 min.

The PCR product was fractionated by electrophoresis in 1.5–2.0% agarose gel before purification of amplified fragment band was cutted out the gel. The fragment was purified by adding 2–3 times v/v of NaI solution (NaI 8M+0.022 M DTT) and sodium phosphate buffer (1M pH 6.0–6.5) and incubated for 5–10 min. at 50–56° C. Glass beads were added to the suspension, mixed , incubated 1–5 min at room temperature and centrifuged 10–30 seconds . The pellet were washed with ethanol buffer(75% of ethanol, 0.01 M Tris-HCI, pH 7.0–7.6, 0.01 M EDTA, pH 8.0–8.5). The DNA was eluted from the glass spheres with buffer (Tris pH 7.0–7.4 10 mM, 1–3 mM EDTA) at 50–56° C. for 1–5 min.

EXAMPLE 2

Cloning (2)

Figure 1:
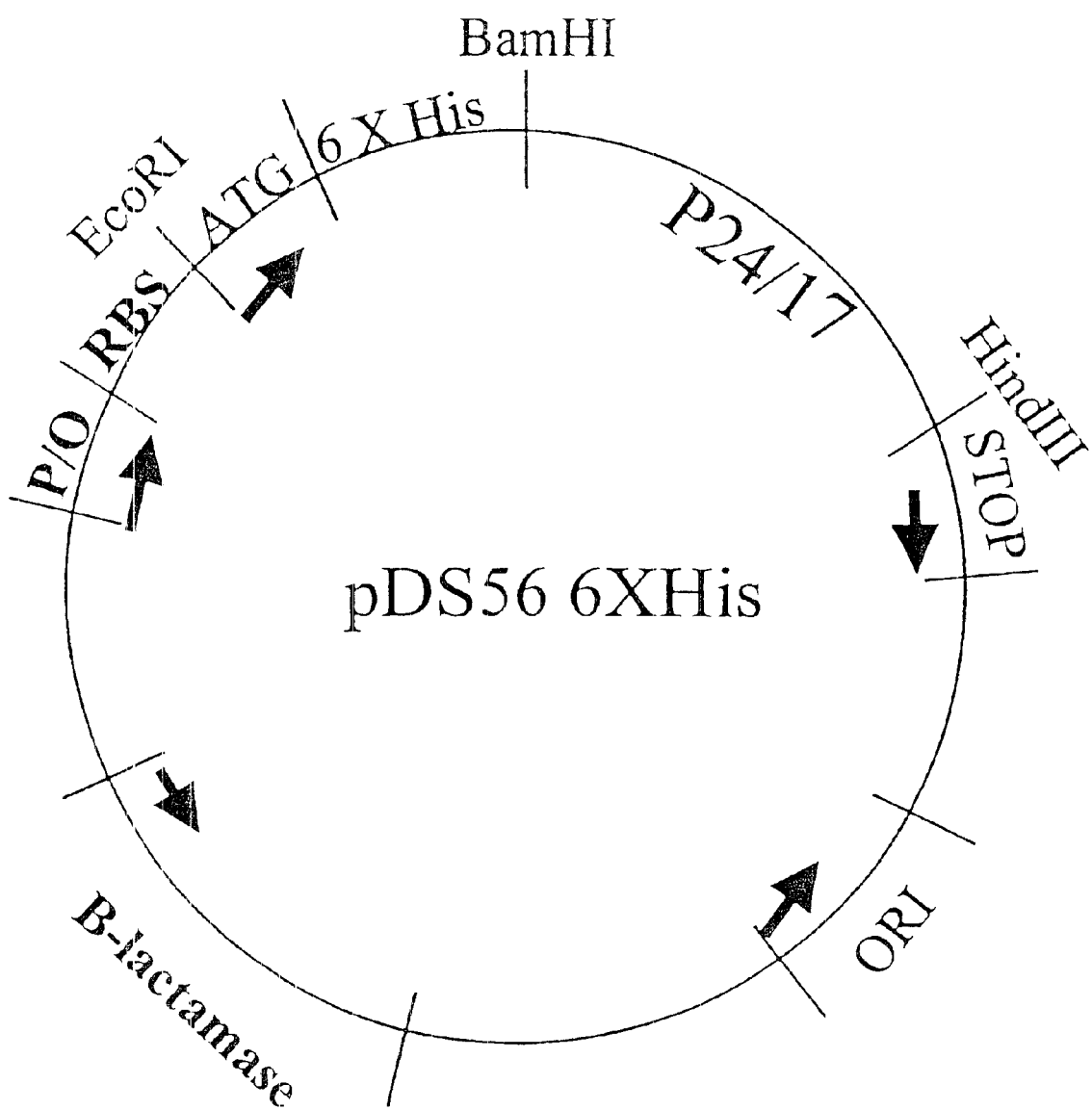
FIG. 1 shows the vector pDS56 used for the expression of the recombinant hybrid p24/p17 protein of HIV-1

The PCR product was digested with enzyme Hind III with 10–20 U of Hind III (Biolabs, England) plus 3–5 I buffer (Promega, EUA) in 30–50 μl volume of $H_2O$. The reactions were incubated at 37° C. for 2–4 h. After this time 10–20 U of Bam HI (Biolabs, England) plus 5–10 μl of react III buffer (BRL, USA) were added to a final 50–100 μl volume of $H_2O$ dd and it was incubated at 37° C. for 2–4 h. For cloning of the PCR product into plasmid PDS-56 (FIG. 1), the vector was digested with 10–20 U of enzyme Hind III(Promega, USA), 2–5 μl buffer I B (Promega,E.U.A.) in 20–50 μl final volume of $H_2O$ , and incubation at 37° C. for 2–4 h. To the reaction was added 10–20 U of the enzyme Bam Hi (Promega, USA), 5–10 μl of react III (BRL, E.U.A), in 50–100 μfinal volume of $H_2O$ , and incubation at 37° C. for 2–4 h. After digestion the DNA was fractionated by electrophoresis in a 1–2% TAE-agarose gel and bands purified as already described.

The ligation reaction was performed by adding 20–50 ng of the DNA fragment insert, 5–15 ng of the vector DNA, plus 0.5–2.0 U of T4 ligase (Promega, USA), 5mM ATP (Promega,E.U.A.), ligation buffer(Promega,E.U.A.), $H_2O$ dd qsp 15 μl, with incubation at 14–16° C. (BOD, FANEN, Brazil) for 12–18 h.

EXAMPLE 3

Transformation (3)

The bacterial transformation was done with *Escherichia coli* by adding the ligation reaction completed to 40–60 μl volume buffer (Tris 10 mM pH 7.2–7.4, EDTA 1 mM) to 100 μl of competent bacteria suspension. The tubes were slightly rotated and immediately incubated on ice bath for 20–40 min. After that, they were submitted to a thermal shock at 40–42° C. for 1–3 min. and kept on ice bath for further 20–40 seconds. LB medium (Bacto triptona 1% p/v, extract of yeast 0.5% p/v, NaCl 171 mM) without antibiotic was added at double volume and incubated at 37° C. for 1–2h. The bacteria were pelleted, homogenized in LB and inoculated in Petri dish plates with LB agar (agar 1.5% p/v, yeast extract 0.5% p/v, triptone 0.1% p/v, NaCl 0.5% p/v pH 7.2–7.5) with 50–200 pg/ml ampicillin and 20–100 pg/ml kanamycin. The plates were incubated at 37° C. for 15–24 h. For the selection of the positive clones they were grown in LB with 50–200 pg/ml ampicillin and 20–100 pg/ml kanamycin at 37° C. under agitation for 15–20 h. After incubation a PCR using specific primers of the vector (for amplification of the area corresponding to insert) being the primer (sense) 5'-TTCATTAAAGAGGAGAAATT-3'(SEQ ID NO. 3) and primer (anti-sense) 5'-CTATCAACAGGAGTCCAAGC-3'(SEQ ID NO. 4). The reaction was made with Taq. polymerase buffer10X (KCl 500 mM, Tris-HCl 100 mM pH 9.0–9.5, $MgCl_2$ 15–25 mM and triton X-100 1–2%), 0.5–1.0 U of Taq polymerase (Promega, USA), 0.5–1.5 mM $MgCl_2$, 20–50 mM of each nucleotide (dATP, dCTP, dGTP, dTTP), 10–30 pmoles of each primer, 0.5–1 μl of bacterial suspension and $H_2$ Odd sterile qsp 20–40 μl.

The reaction was processed with 1–3 cycles of 94–96° C./5 min., 50–55° C./1–2 min., 70–72° C./1–2 min., 30 cycles of 94–96° C./30–45 seg., 45–50° C./30–45 seg., 70–72° C./30–45 seg. and 1 cycle of 94–96° C./1–2 min., 45–50° C./1–2 min., 70–72° C./10–15 min. The of this reaction was fractionated through 1–2%. agarose gel electrophoresis.

EXAMPLE 4

Sequencing (4)

Figure 3:
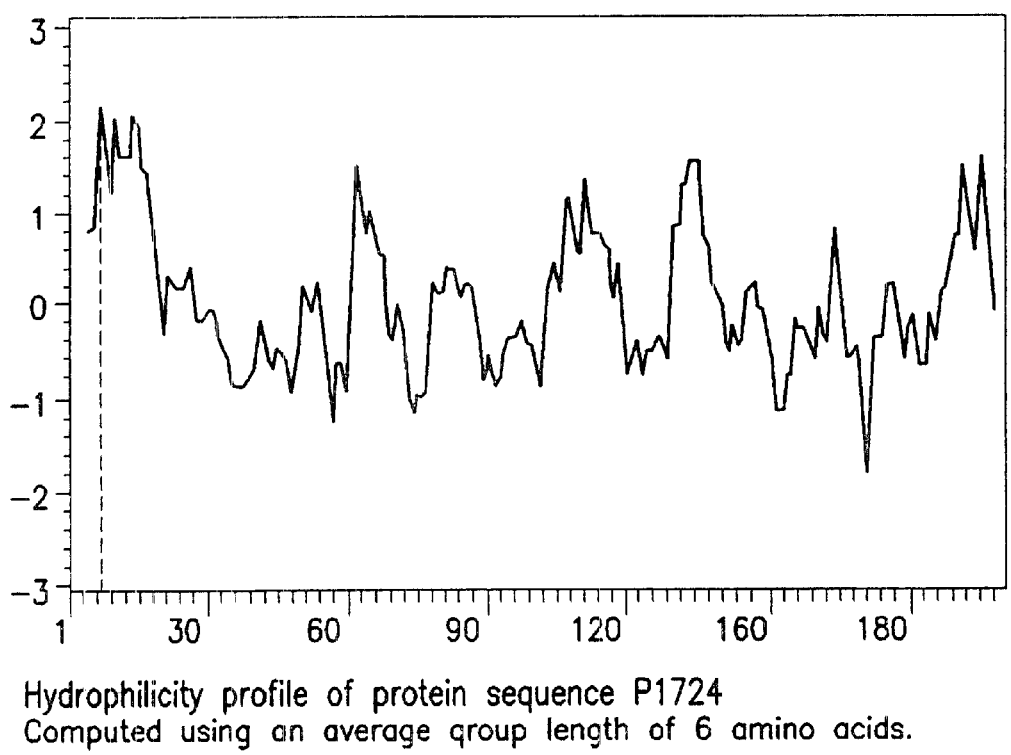
FIG. 3 shows the hydrofilicity profile from the recombinant hybrid p24/p17 protein of HIV-1

The positive clones were sequenced to confirm the sequence of FIG. 2 and presents the hydrofilicity profile as showed in FIG. 3.

EXAMPLE 5

Protein production (5)

Figure 4:
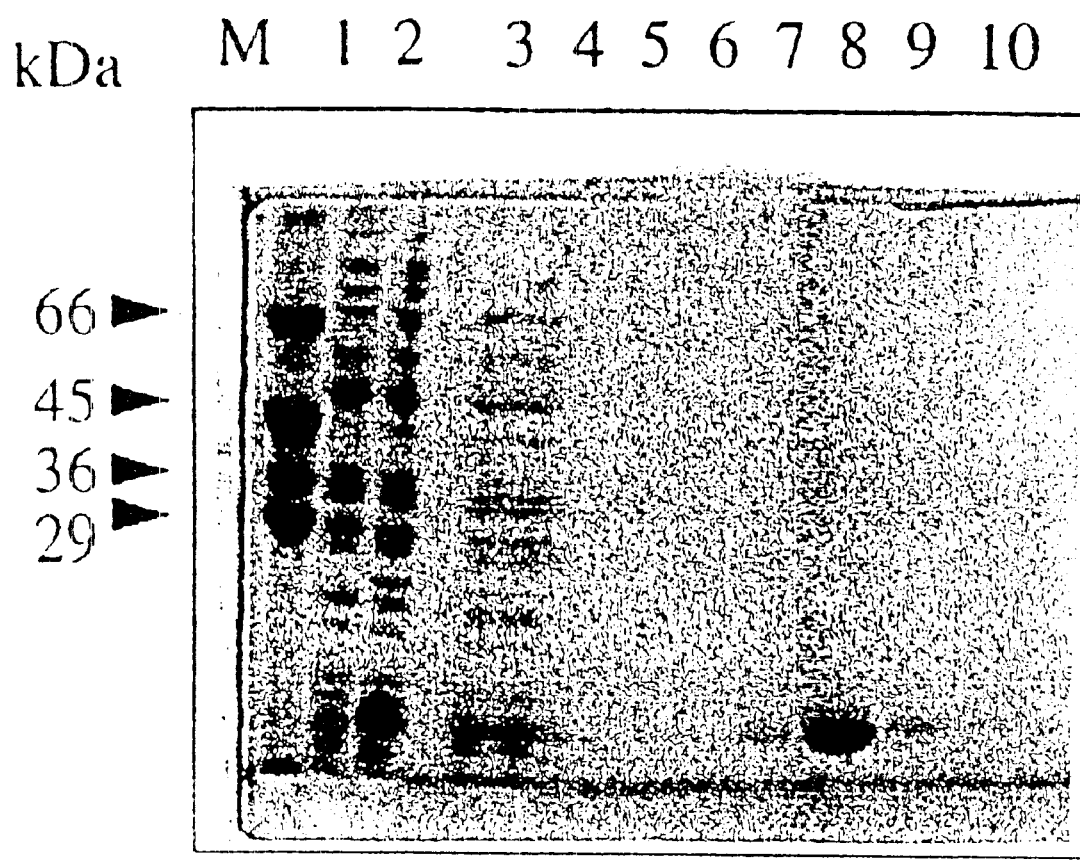
FIG. 4 shows a PAGE with the purified recombinant hybrid p24/p17 protein of HIV-1

The positive clones were used for production of protein and they were grown in LB medium with 50–200 μg/ml ampicillin, 50–200 of Kanamycin μg/ml and incubated at 37° C. under agitation until the optical density (OD 600 nm) of 0.5–0.7. Then, for the induction of the protein, IPTG (Isopropyl-□-D-thiogalactpyranoside) to 0.2–0.4 M was added and incubated for 3–5 h. The bacteria were centrifuged, the supernatant was discarded and the pellet homogenized in buffer A (guanidine-HCl 5–6 M, sodium phosphate 0.1–0.2 M, Tris 0.01–0.02 M pH 7.8–8.0) with agitation for 1–2 h. A polyacrylamide gel shows the expression in the bacteria. (FIG. 4)

EXAMPLE 6

Protein purification (6)

After the centrifugation the supernatant was applied to a column with Ni-NTA (nickel chelate) resin. For purification of the protein the column was washed sequentially with buffer A, buffer B (Urea 7–8 M, phosphate of sodium 0,1–0,2 M, Tris 0.01–0.02 M pH 7.8–8.0) and with buffer C (Urea 7–8 M, phosphate of sodium 0.1–0.2 M, Tris 0.01–0.02 M pH 7.0–7.2). The protein was eluted with buffer D (Urea 7–8 M, sodium phosphate 0.1–0.2 M, Tris 0.01–0.02 M pH 5.0–5.2) and sequentially with urea 7–8 M, phosphate of sodium 0.1–0.2 M, Tris 0.01–0.02 M pH 40–4.2. Fractions were collected and 50 µl of each fraction was diluted v/v in sample buffer, heated for 10 min. and submitted to electrophoresis in polyacrylamide gel (SDS-PAGE).

While the present invention has been described in connection with examples, it will be understood that modifications and variations apparent to those ordinary skill in the art are within the scope of the present invention.

What is claimed is:

1. A recombinant hybrid p24/p17 protein of HIV-1 consisting of SEQ ID NO. 5.

* * * * *